US008603135B2

(12) United States Patent
Mueller (10) Patent No.: US 8,603,135 B2
(45) Date of Patent: Dec. 10, 2013

(54) ARTICULATING SURGICAL APPARATUS (75) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 91 days.

(21) Appl. No.: 13/186,686

(22) Filed: Jul. 20, 2011

(65) Prior Publication Data

US 2013/0023915 A1  Jan. 24, 2013

(51) Int. Cl.
*A61B 17/00* (2006.01)
(52) U.S. Cl.
USPC .................................. 606/205; 606/170
(58) Field of Classification Search
USPC ............... 606/1, 108, 170, 174, 205–209; 604/528; 138/120, 119, 112; 600/139–153
See application file for complete search history.

(56) References Cited

U.S. PATENT DOCUMENTS

| 2,823,703 | A | * | 2/1958 | Nusser, Jr. ................. 285/181 |
| 2,956,248 | A | * | 10/1960 | Strand ......................... 333/241 |
| 3,306,634 | A | | 2/1967 | Groves et al. |
| 3,497,083 | A | * | 2/1970 | Anderson et al. ............ 414/738 |
| 3,895,636 | A | * | 7/1975 | Schmidt ........................ 606/205 |
| 5,176,126 | A | * | 1/1993 | Chikama ....................... 600/139 |
| 5,248,170 | A | * | 9/1993 | Francis .......................... 285/114 |
| 5,374,277 | A | | 12/1994 | Hassler |
| 5,417,203 | A | | 5/1995 | Tovey et al. |
| 5,476,479 | A | | 12/1995 | Green et al. |
| 5,483,952 | A | | 1/1996 | Aranyi |
| 5,501,654 | A | | 3/1996 | Failla et al. |
| 5,601,572 | A | | 2/1997 | Middleman et al. |
| 5,609,601 | A | | 3/1997 | Kolesa et al. |
| 5,673,840 | A | | 10/1997 | Schulze et al. |
| 5,704,534 | A | | 1/1998 | Huitema et al. |
| 5,762,067 | A | | 6/1998 | Dunham et al. |
| 5,778,939 | A | * | 7/1998 | Hok-Yin ....................... 138/120 |
| 5,820,009 | A | | 10/1998 | Melling et al. |
| 5,823,066 | A | | 10/1998 | Huitema et al. |
| 5,860,995 | A | | 1/1999 | Berkelaar |
| 5,904,667 | A | | 5/1999 | Falwell |
| 6,063,098 | A | | 5/2000 | Houser et al. |
| 6,083,234 | A | | 7/2000 | Nicholas et al. |
| 6,800,056 | B2 | * | 10/2004 | Tartaglia et al. ............. 600/114 |
| 7,008,375 | B2 | * | 3/2006 | Weisel .......................... 600/141 |
| 7,533,906 | B2 | | 5/2009 | Luettgen et al. |
| 7,543,518 | B2 | * | 6/2009 | Buckingham et al. ..... 74/490.05 |
| 7,588,176 | B2 | | 9/2009 | Timm et al. |
| 7,588,546 | B2 | | 9/2009 | de Andrade |
| 7,588,575 | B2 | | 9/2009 | Colleran et al. |
| 7,608,081 | B2 | | 10/2009 | Abdelgany |
| 7,615,067 | B2 | | 11/2009 | Lee et al. |
| 7,618,442 | B2 | | 11/2009 | Spitler et al. |
| 7,637,410 | B2 | | 12/2009 | Marczyk |
| 7,670,334 | B2 | | 3/2010 | Hueil et al. |
| 7,678,117 | B2 | * | 3/2010 | Hinman et al. ............... 606/108 |
| 7,699,835 | B2 | * | 4/2010 | Lee et al. ......................... 606/1 |

(Continued)

*Primary Examiner* — Ryan Severson
*Assistant Examiner* — David Eastwood (57) ABSTRACT An endoscopic instrument includes a housing having shaft. The shaft includes an articulating section disposed thereon. The articulating section includes a plurality of annular stationary and rotatable links arranged in an alternating configuration therealong. Each link of the plurality of rotatable links seated within a corresponding stationary link of the plurality of stationary links to collectively define a central annulus therethrough. An end effector assembly operatively connected to a distal end of the shaft includes a pair of first and second jaw members. An articulation catheter operably disposed through the central annulus is configured to rotate the rotatable links with respect to the stationary links to articulate the shaft about the articulating section.

19 Claims, 7 Drawing Sheets

(56) References Cited

U.S. PATENT DOCUMENTS

| | | |
|---|---|---|
| 7,789,283 B2 | 9/2010 | Shah |
| 7,819,296 B2 | 10/2010 | Hueil et al. |
| 7,819,297 B2 | 10/2010 | Doll et al. |
| 7,819,298 B2 | 10/2010 | Hall et al. |
| 7,824,411 B2 | 11/2010 | Varieur et al. |
| 7,824,413 B2 | 11/2010 | Varieur et al. |
| 7,832,612 B2 | 11/2010 | Baxter, III et al. |
| 7,837,080 B2 | 11/2010 | Schwemberger |
| 7,842,044 B2 | 11/2010 | Runco et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,887,539 B2 | 2/2011 | Dunbar, Jr. et al. |
| 7,887,541 B2 | 2/2011 | Runco et al. |
| 7,905,380 B2 | 3/2011 | Shelton, IV et al. |
| 7,905,381 B2 | 3/2011 | Baxter, III et al. |
| 7,905,907 B2 | 3/2011 | Spitler et al. |
| 7,922,061 B2 | 4/2011 | Shelton, IV et al. |
| 7,931,677 B2 | 4/2011 | Abdelgany |
| 7,934,630 B2 | 5/2011 | Shelton, IV et al. |
| 2002/0062131 A1* | 5/2002 | Gallo, Sr. .................. 606/167 |
| 2002/0120178 A1* | 8/2002 | Tartaglia et al. ............ 600/114 |
| 2002/0165580 A1* | 11/2002 | Zwiefel et al. ............... 606/205 |
| 2003/0149338 A1* | 8/2003 | Francois et al. ............. 600/152 |
| 2004/0236316 A1* | 11/2004 | Danitz et al. .................. 606/1 |
| 2005/0149048 A1 | 7/2005 | Leport et al. |
| 2006/0178556 A1 | 8/2006 | Hasser et al. |
| 2006/0199999 A1* | 9/2006 | Ikeda et al. ................ 600/141 |
| 2007/0027468 A1 | 2/2007 | Wales et al. |
| 2007/0219550 A1 | 9/2007 | Thompson et al. |
| 2007/0221701 A1 | 9/2007 | Ortiz et al. |
| 2007/0225562 A1 | 9/2007 | Spivey et al. |
| 2008/0039776 A1 | 2/2008 | Ghabrial et al. |
| 2009/0023986 A1 | 1/2009 | Stewart et al. |
| 2009/0065549 A1 | 3/2009 | Viola |
| 2009/0088792 A1 | 4/2009 | Hoell, Jr. et al. |
| 2009/0125019 A1 | 5/2009 | Douglass et al. |
| 2009/0137984 A1 | 5/2009 | Minnelli |
| 2010/0030018 A1 | 2/2010 | Fortier et al. |
| 2010/0057121 A1 | 3/2010 | Piskun et al. |
| 2010/0126616 A1* | 5/2010 | Kanao ......................... 138/122 |
| 2010/0160736 A1* | 6/2010 | Padget et al. ................ 600/142 |
| 2010/0179540 A1 | 7/2010 | Marczyk et al. |
| 2010/0298638 A1 | 11/2010 | Slater |
| 2010/0298854 A1 | 11/2010 | Slater |
| 2011/0295065 A1* | 12/2011 | Gurusamy et al. .......... 600/114 |
| 2012/0012220 A1* | 1/2012 | Perry .......................... 138/120 |
| 2012/0197241 A1* | 8/2012 | Golden et al. ................. 606/1 |

\* cited by examiner

ARTICULATING SURGICAL APPARATUS

BACKGROUND

1. Technical Field

The present disclosure relates to an articulating surgical apparatus. More particularly, the present disclosure relates to an articulating surgical apparatus including an articulating section configured to lock the surgical apparatus in a non-articulated configuration.

2. Description of Related Art

Surgical instruments that are configured to articulate or bend are well known in the medical arts. Surgical instruments of this nature are utilized in many surgical procedures. For example, laparoscopic, endoscopic, or other minimally invasive surgical procedures are just a few of the many surgical procedures where articulating surgical instruments may find use. When utilized in such procedures, the surgical instruments may include a housing, a handle assembly, an articulating shaft, a device for articulating the shaft, and an end effector including a pair of jaw members.

As can be appreciated, the relatively small operable working space that is created within a cavity of a patient during a surgical procedure often makes it difficult for the surgeon to position the jaw members adjacent or close to target tissue. The articulating shaft allows a surgeon to position the jaw members adjacent target tissue.

Various articulating devices or mechanisms may be utilized to articulate the shaft. For example, some surgical instruments utilize one or more articulating cables or tendons that couple to one or more articulation links on the shaft. Typically, the cables or tendons provide a mechanical interface from the one or more articulation links to an actuation device, e.g., rotatable dials, disposed on the housing and/or handle assembly of the surgical instrument such that actuation of the actuation device moves or articulates the shaft about the articulation links. In particular, the cables or tendons are "pulled" or otherwise manipulated via one or more mechanisms in the handle assembly or the housing to articulate the shaft about the articulating links.

Under certain surgical scenarios, it may prove advantageous to maintain the shaft in a relatively fixed or stationary position, such as, for example, when positioning tissue between the jaw members or when the shaft is inserted through a trocar or cannula. Locking the cables or tendons so that the shaft is prevented from articulating typically requires eliminating, what is commonly referred to in the art as, cable or tendon "stretch" from the cables or tendons. Cable or tendon "stretch" is the ability of the cable or tendon to stretch under a predetermined load. To remove this cable or tendon stretch, the cables or tendons are typically highly loaded in tension. Removing this cable or tendon stretch limits and/or eliminates "post lock" articulation. However, due to the length of the surgical instrument and, thus, the corresponding length of the cables or tendons between the articulating links and the actuation device and/or locking device, a fairly large "spring rate" exists with a corresponding "stiffness" penalty being observed. That is, overtime, subjecting the cables or tendons to high load tension reduces the stiffness of the cables or tendons and, thus, the overall stiffness of the shaft. As can be appreciated, reducing the "stiffness" of the shaft may result in the shaft not functioning in a manner as intended.

SUMMARY

The present disclosure provides an endoscopic instrument. The endoscopic instrument includes a housing having shaft extending therefrom that defines a longitudinal axis therethrough. The shaft includes an articulating section disposed thereon. The articulating section having a plurality of stationary and rotatable links arranged in an alternating configuration along the articulating section. Each link of the plurality of rotatable links rotatably seat within a corresponding stationary link of the plurality of stationary links to collectively define a central annulus therethrough. An end effector assembly operatively connected to a distal end of the shaft for effecting tissue and includes a pair of first and second jaw members. An articulation catheter operably disposed through the central annulus is configured to rotate the rotatable links with respect to the stationary links to articulate the shaft about the articulating section.

The present disclosure provides an endoscopic forceps. The endoscopic instrument includes a housing having shaft extending therefrom that defines a longitudinal axis therethrough. The shaft includes an articulating section disposed thereon. The articulating section having a plurality of stationary and rotatable links arranged in an alternating configuration along the articulating section. Each link of the plurality of rotatable links rotatably seat within a corresponding stationary link of the plurality of stationary links to collectively define a central annulus therethrough. An end effector assembly operatively connected to a distal end of the shaft includes a pair of first and second jaw members. One or both of the first and second jaw members is movable relative to other jaw member from an open position, wherein the first and second jaw members are disposed in spaced relation relative to one another, to a clamping position, wherein the first and second jaw members cooperate to grasp tissue therebetween. An articulation catheter operably disposed through the central annulus is configured to rotate the rotatable links with respect to the stationary links to rotate the rotatable links with respect to the stationary links to articulate the shaft about the articulating section. The articulating catheter is configured to house a drive wire that is operably coupled to a cutting element in operable communication with the first and second jaw members. The drive wire translatable within the articulating catheter to translate the cutting element longitudinally through at least one of first and second jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to the end of a surgical instrument that is closer to the user, while the term "distal" will refer to the end of the surgical instrument that is farther from the user.

Figure 1:
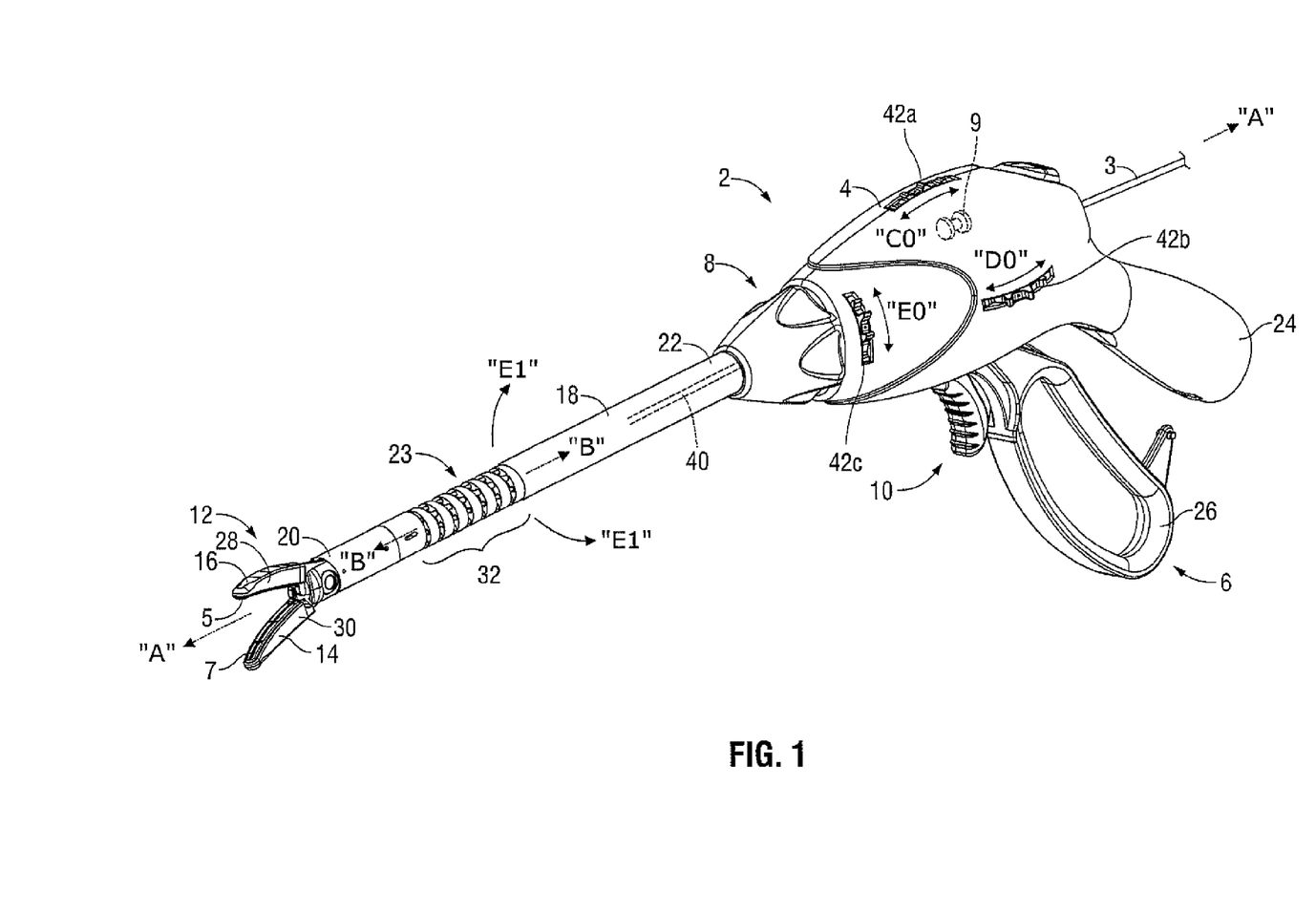
FIG. 1 is a side, perspective view of an endoscopic instrument in an non-articulated configuration according to an embodiment of the present disclosure.
Figure 2:
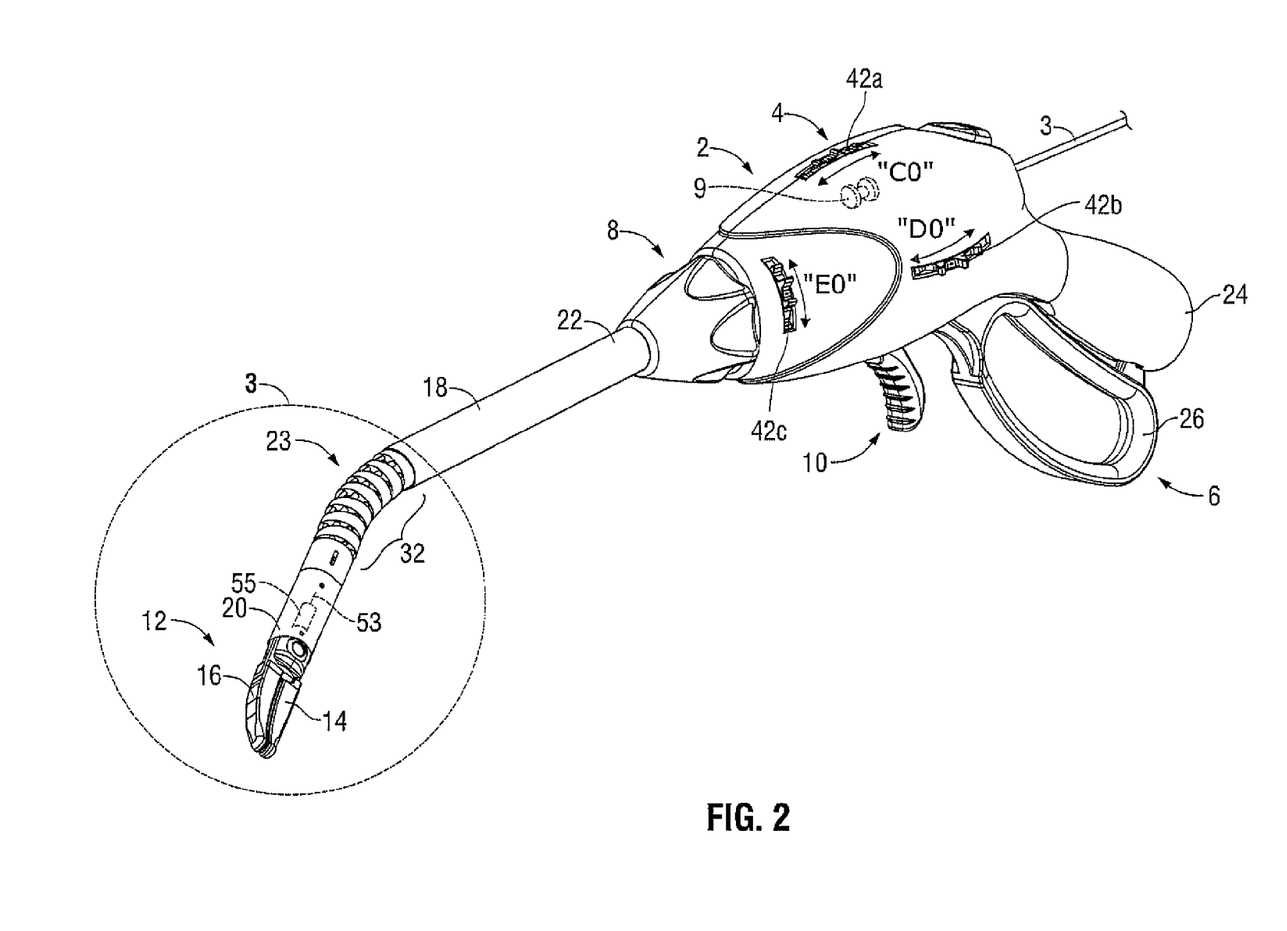
FIG. 2 is a side, perspective view of the endoscopic instrument depicted in FIG. 1 shown in an articulated configuration.

With reference to FIGS. 1-8B, and with initial reference to FIGS. 1 and 2, an illustrative embodiment of an articulating surgical instrument, e.g., an articulating endoscopic instrument, such as, for example, an articulating endoscopic forceps 2 (forceps 2), is shown. As can be appreciated, other types of articulating instruments that are configured to treat tissue may be utilized in accordance with the present disclosure, e.g., snares, blades, loops, stabilizers, retractors, etc.

Forceps 2 is adapted to couple to an electrosurgical generator (not shown) configured for performing an electrosurgical procedure. An electrosurgical procedure may include sealing, cutting, cauterizing, coagulating, desiccating, and fulgurating tissue all of which may employ RE energy. The electrosurgical generator may be configured for monopolar and/or bipolar modes of operation. The electrosurgical generator may include or is in operative communication with one or more processors (not shown) in operative communication with the one or more control modules that are executable on the one or more processors. The control module may be configured to instruct one or more modules to transmit electrosurgical energy, which may be in the form of a wave or signal/pulse, via one or more cables (e.g., an electrosurgical cable 3) to one or both seal plates 5, 7 disposed on respective jaw housings 28 and 30. However, in certain embodiments, the forceps 2 may be battery powered.

Continuing with reference to FIGS. 1 and 2, forceps 2 is shown configured for use with various electrosurgical procedures and generally includes a housing 4, an electrosurgical cable 3 that connects the forceps 2 to an electrosurgical generator, a handle assembly 6, a rotating assembly 8, a trigger assembly 10, a drive assembly 9, and an end effector assembly 12 that operatively connects to the drive assembly 9. The drive assembly 9 may be in operative communication with handle assembly 6 for imparting movement of one or both of a pair of jaw members 14, 16 of end effector assembly 12.

For a more detailed description of the forceps 2 including rotating assembly 8, trigger assembly 10, and electrosurgical cable 3 (including line-feed configurations and/or connections), reference is made to commonly owned U.S. Pat. Publication No. 2007/0173814 filed on Nov. 9, 2006.

With continued reference to FIGS. 1 and 2, housing 4 is illustrated. Housing 4 is accessible by a surgeon from outside a body cavity to control the positioning, orientation and operation of the end effector 12 when the end effector 12 is positioned inside a body cavity at a surgical site. To provide this operability, the housing 4 supports various components that are operable to induce or prohibit movement in the end effector 12 through various modes. More particularly housing 4 is configured to house or support handle assembly 6, drive assembly 9 and dials 42a, 42b and a catheter rotation dial 42c.

Dials 42a and 42b operably couple to a plurality of cables or tendons 34 (FIGS. 3-5) that are in operative communication with an articulating section 23 of the shaft 18, as described in greater detail below. Articulation dial 42a may be rotated in the direction of arrow "C0" to tension one or more of a plurality of tendons 34. Similarly, articulation dial 42b may be rotated in the direction of arrow "D0" to tension one or more of a plurality of tendons 34. Rotation of the articulation dials 42a and 42b in either direction of arrows "C0" or "D0" provides a tensioning or "stiffening" effect to the plurality of tendons 34 to facilitated locking the shaft 12 about the articulating section 23.

Catheter rotation dial 42c (FIGS. 1 and 2) is operable to rotate a rotation catheter 37 (FIGS. 3-5) to various rotated orientations with about the axis "A-A" defined through the shaft 18. More particularly, catheter rotation dial 42e may be rotated in the direction of arrow "E0" to induce rotational movement as indicated by arrow "E1," see FIG. 1. Rotation of the articulating dial 42c in either a clockwise or counter-clockwise articulates the shaft 18 to one or more orientations about the articulating section 23, see FIG. 2. In one particular embodiment, rotating the catheter rotation dial 42c 180° in either the clockwise or counter clockwise direction articulates the shaft 18 to an end position that is in a horizontal plane that is approximately 90° about the axis "A-A", i.e., the shaft 18 will be positioned 90° to the left or right of the axis "A-A."

Shaft 18 includes a generally elongated configuration and defines the axis "A-A" therethrough, FIG. 1. Shaft 18 has a distal end 20 configured to mechanically engage the end effector assembly 12 and a proximal end 22 that mechanically engages the housing 4 (FIGS. 1 and 2).

With reference to FIGS. 1-5, an articulating portion or section 23 is operably disposed on or coupled to the shaft 18 between the proximal and distal ends 22 and 20, respectively. The articulation section 23 is defined by a plurality of stationary links 32a (links 32a) and a plurality of rotatable links 32b (links 32b), FIGS. 3-7. The links 32a and 32b are operable to articulate the shaft 18 transversely across the axis "A-A" in either the horizontal or vertical plane. For illustrative purposes, the shaft 18 is shown articulated across the horizontal plane, see FIGS. 2 and 4. Moreover, the links 32a and 32b are operable to maintain the shaft 18 in one or more locked positions about the axis "A-A," described in more detail below.

Each stationary link of the links 32a is identical to one another. Likewise, each rotatable link of the links 32b is identical to one another. In view thereof, and for illustrative purposes, the specific components of each stationary link of the links 32a is described with specific reference to a stationary link 32a' (hereinafter simply link 32a', see FIG. 6), and the specific components of each rotatable link of the links 32b is described with specific reference to a rotatable link 32b' (hereinafter simply link 32b', see FIG. 7). Link 32b' functions as a "swash earn" and the link 32a' functions as a "cam follower." That is, the link 32a' tilts about a rotation catheter 37 as a result of the link 32b' rotating about the rotation catheter 37; the significance of which is described below.

Figure 6:
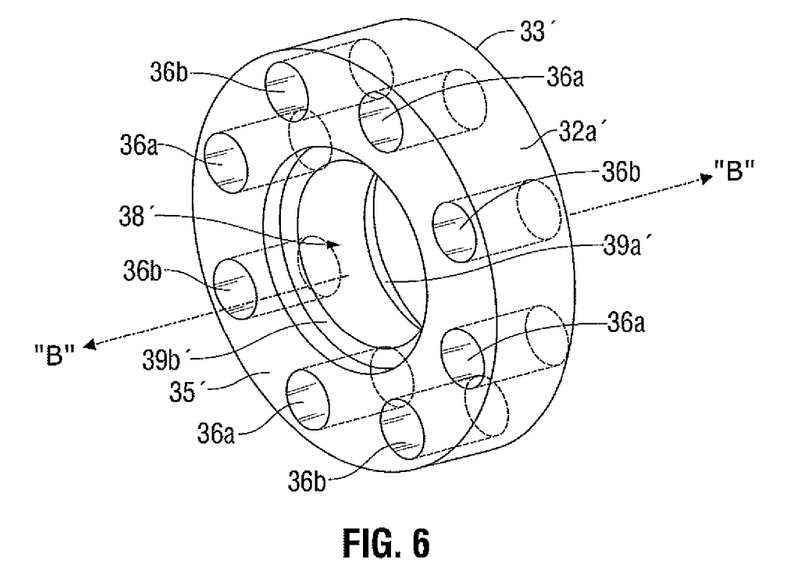
FIG. 6 is a perspective view of a stationary link of an articulating section of the endoscopic instrument depicted in FIG. 1.

Continuing with reference to FIG. 6, link 32a' is illustrated. Link 32a' may be made from any suitable material including, but not limited to plastics, plastic composites, ceramics, metals, and metal alloys. In the illustrated embodiment, link 32a' is made from surgical steel.

Link 32a' includes a proximal face 33' and a distal face 35' (FIGS. 3-6). The proximal face 33' is proximal to the housing 4, i.e., faces a user, see FIG. 3 for example. Proximal face 33' is also perpendicular to the axis "A-A" and an axis "B-B" defined through an annulus 38' of the link 32a' (FIG. 6). The distal face 35' is oriented at one or more suitable angles with respect to the proximal face 33' (FIG. 6). In the illustrated embodiment, distal face 35' is orientated with respect to the proximal face 33' at an angle that ranges from about 1° to about 15°. The specific orientation of the distal face 35' with respect to the axis "A-A", axis "B-B" and/or annulus 38' may be varied during manufacture thereof to accommodate specific locking angles of the distal face 35' of the link 32a'. To facilitate maintaining the shaft 18 in a non-articulated configuration, i.e., maintaining the shaft 18 along the axis "A-A", the distal face 35' of each link 32a' are aligned parallel with respect to corresponding links 32a' (FIG. 1).

The proximal and distal faces 33' and 35' of link 32a' each includes a respective counter bore 39a' and 39b' that is concentric to the proximal and distal faces 33' and 35', respectively, for interfacing with link 32b' (FIG. 6), described in greater detail below. In the illustrated embodiment, the counter bores 39a' and 39b' on each of the respective proximal and distal faces 33' and 35' include the same depth and diameter. As can be appreciated, the depth and diameter may be varied to accommodate an end user's and/or manufacturers' specific needs.

Figure 7:
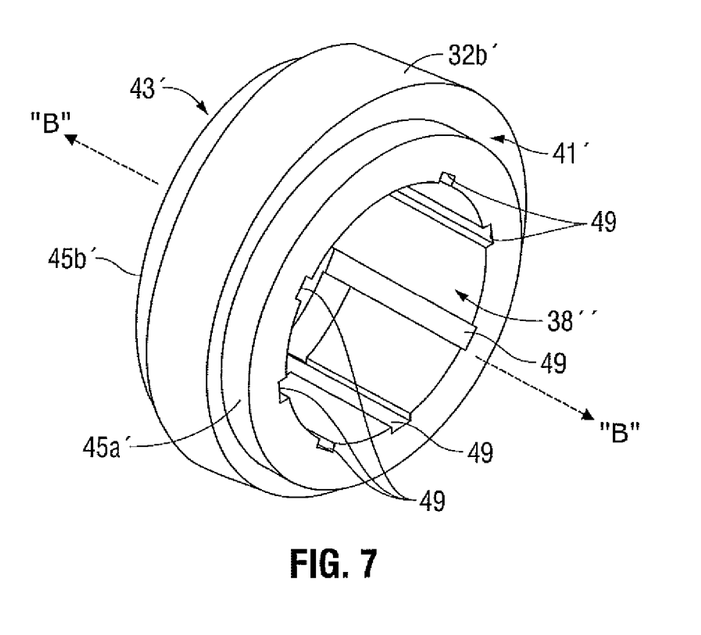
FIG. 7 is a perspective view of a rotating link of the articulating section of the endoscopic instrument depicted in FIG. 1.

With reference to FIG. 7, link 32b' is illustrated. Link 32b' may be made from one or more of the materials described above with respect to link 32a'. In the illustrated embodiment, the link 32b' is made from a rigid plastic.

Link 32b' is rotatable from a first configuration that allows articulation of the shaft 18 about the articulating section 23, to a second configuration that "locks" the shaft 18 and prevents articulation thereof about the articulating section 23. Link 32b' includes a proximal face 41' and a distal face 43' (FIG. 7). The proximal face 41' is disposed adjacent the proximal face 33' of the link 32a and perpendicular to the axis "A-A" and axis "B-B" defined through an annulus 38" of the link 32b' (FIG. 7). The distal face 43' is disposed adjacent the distal face 35' and oriented at one or more suitable angles with respect to the proximal face 41' (FIG. 7). As described above with respect to proximal face 33' of link 32a', the specific orientation of the distal face 43' with respect to the axis "A-A," axis "B-B" and/or annulus 38" may be varied during manufacture thereof to accommodate a specific locking angle of the distal face 43' of the link 32b'. In the illustrated embodiment, distal face 43' is orientated at an angle that ranges from about 1° to about 15° with respect to the proximal face 41'. The angle of the distal face 43' is equal to the angle of the distal face 35' of the link 32a' such that in an "unlocked" configuration, i.e., the shaft 18 is able to articulate, the distal faces 43' and 35' are in substantial contact with and parallel to one another, see FIG. 8A. In a "locked" configuration, i.e., the shaft 18 is unable to articulate, the distal faces 43' and 35' are coincident to one another.

Figure 8A:
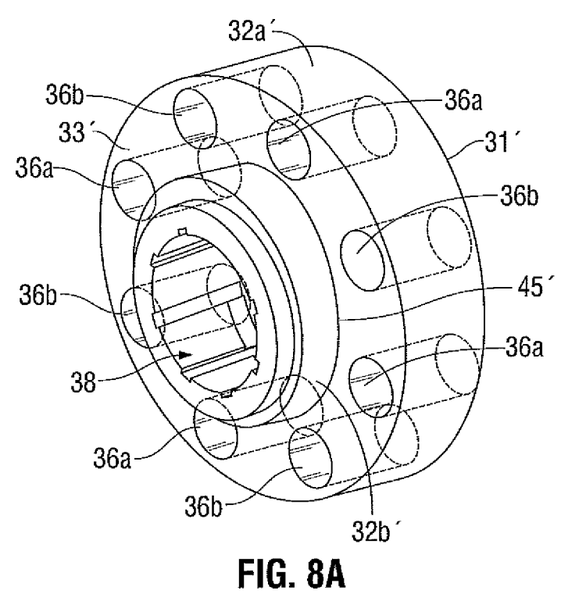
FIG. 8A is a perspective view of the stationary link depicted in FIG. 6 and the rotating link depicted in FIG. 7 coupled to one another and in an unlocked configuration.
Figure 8B:
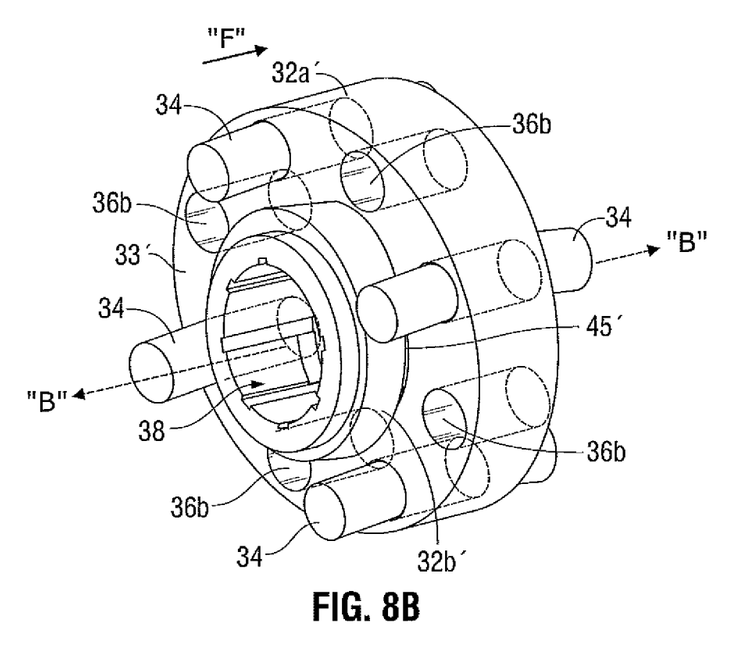
FIG. 8B is a perspective view of the stationary link depicted in FIG. 6 including a plurality of tendons extending therethrough and the rotating link depicted in FIG. 7 coupled to one another and in a locked configuration.

The proximal and distal faces 41' and 43' of link 32b' include a respective boss 45a' and 45b' (FIG. 6) that is concentric to the proximal and distal faces 41' and 43', respectively, for interfacing with counter bores 39a' and 39b' of link 32a,' see FIGS. 8A and 8B. In the illustrated embodiment, the bosses 45a' and 45b' on each of the respective proximal and distal faces 41' and 43' include the same depth and diameter as each other and the counter bores 39a' and 39b' of link 32a'.

Figure 3:
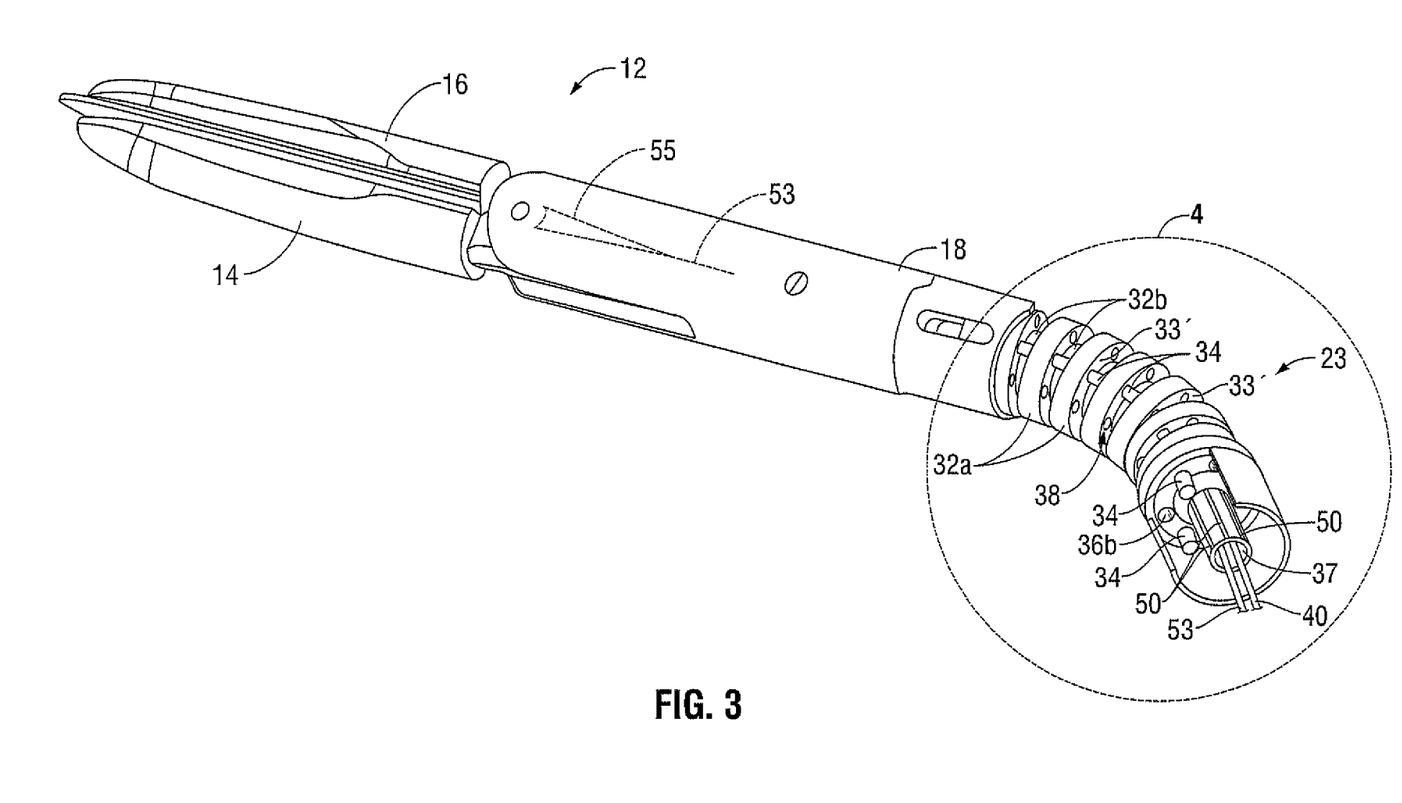
FIG. 3 is an enlarged area of detail depicted in FIG. 2.
Figure 4:
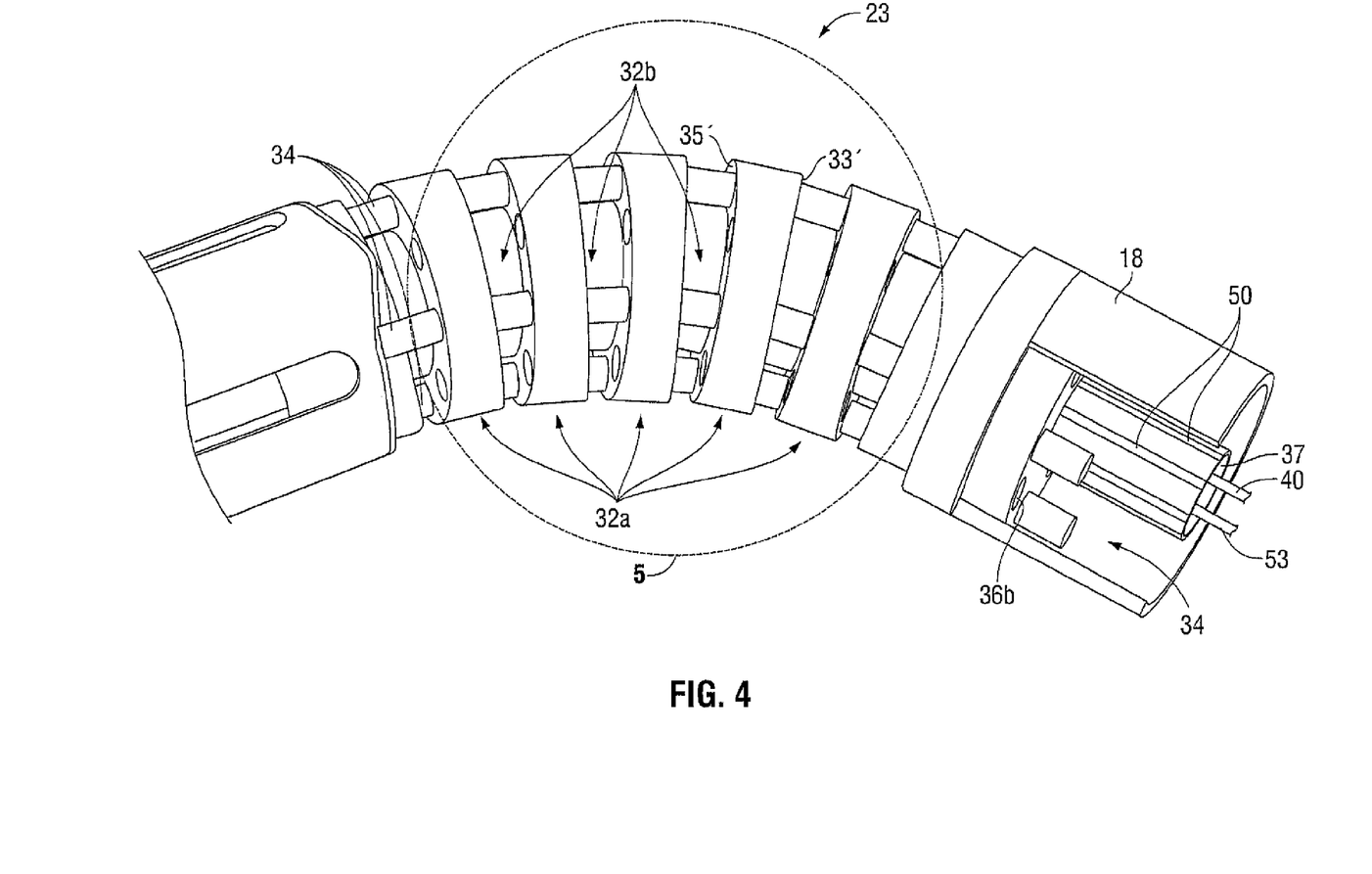
FIG. 4 is an enlarged area of detail depicted in FIG. 3.
Figure 5:
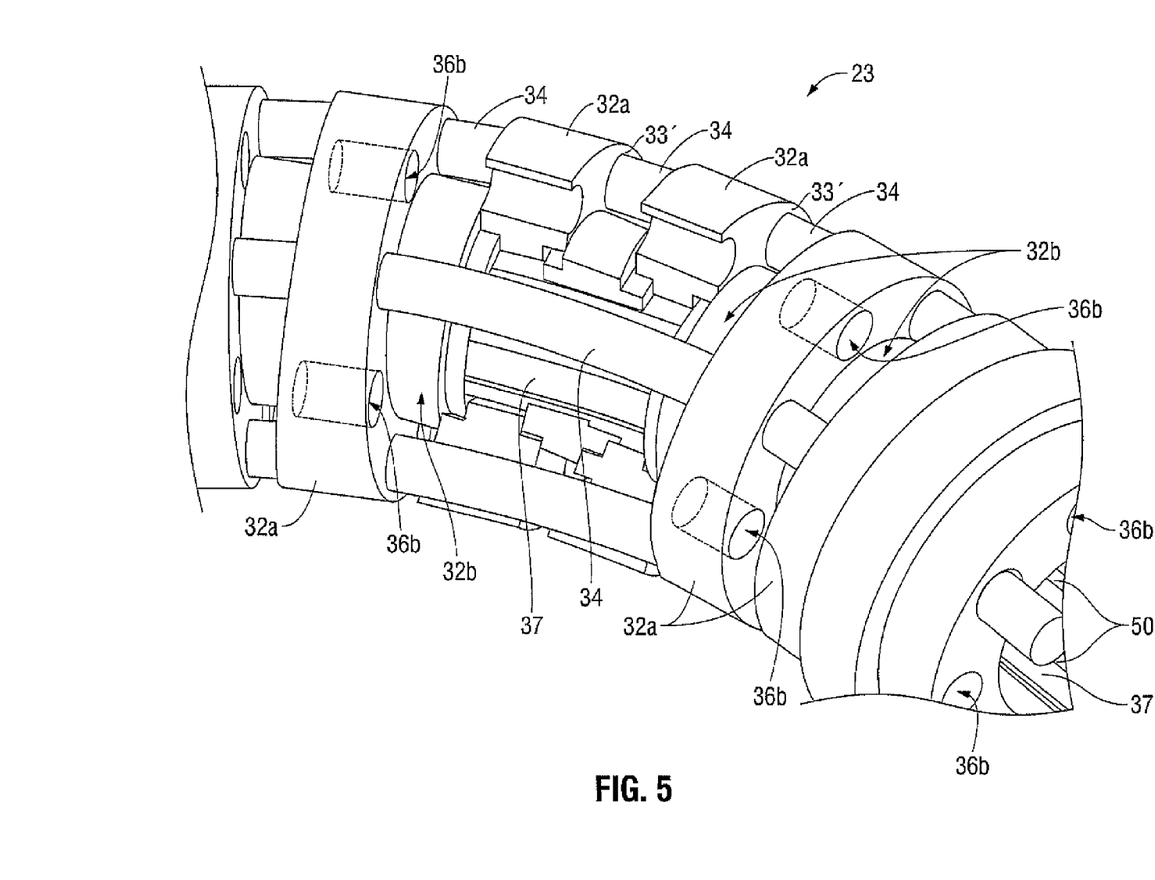
FIG. 5 is a partial cut-away view of an enlarged area of detail depicted in FIG. 4.

Each of the links 32a' and 32b' is cylindrical about its outer diameter, FIGS. 6 and 7. However, to facilitate positioning the link 32b' within the relative small area of the articulating section 23, the outer diameter of the link 32b' is smaller than that of a diameter formed by the tendons 34 such that the links 32b are positionable within the tendons 34, as best seen in FIGS. 3-5.

In accordance with the present disclosure, the angles of the distal faces 35' and 43' may be the same as or different from each other to achieve a specific purpose, i.e., a specific end articulation position. For example, and in the illustrated embodiment, the angles of each of the distal faces 35' and 43' of the links 32a' and 32b' throughout the articulating section 23 are equal to one another and an angle of articulation, i.e., approximately 15°. In other embodiments, the angles of the distal faces 35' and 43' for a given pair (or set) of links 32a' and 32b' may be different from one another. For example, the angles of the distal faces 35' and 43' of links 32a' and 32b' that are positioned at a proximal end of the articulating section 23 may be different from the angles of the distal faces 35' and 43' links 32a' and 32b' that are positioned at a distal end of the articulating section 23. Thus, the resultant articulation angle for the respective proximal and distal ends of the articulating section 23 will be different.

The annuluses 38' and 38" of the links 32a' and 32b', respectively, collectively define a central annulus 38 (see FIGS. 3-5 in combination with FIGS. 8A and 8B) through the articulating section 23 and are configured to receive a catheter rotation tube 37 that is configured to house a drive mechanism, e.g., a drive rod 40 (FIGS. 3-5), therethrough. As can be appreciated, the configuration of the central annulus 38 provides adequate clearance for catheter rotation tube 37 including the drive rod 40 (or other suitable device) therethrough. The central annulus 38 defines the longitudinal axis "B-B" therethrough that is parallel to the axis "A-A" when the shaft 18 is in a non-articulated configuration, see FIG. 1 in combination with FIGS. 6 and 7.

With reference again to FIG. 7, one or more grooves 49 of suitable configuration are defined on an interior surface of link 32b'. In the embodiment illustrated in FIG. 7, a plurality of grooves 49 is defined on an interior surface of link 32b'. For illustrative purposes, seven (7) grooves 49 are illustrated in the representative drawings. Grooves 49 extend longitudinally along the interior surface of the link 32b' and are disposed parallel to the axis "B-B." The grooves 49 are configured to engage a corresponding tongue or spline 50 that is operably disposed on the articulating catheter 37 (FIGS. 4 and 5). In certain embodiments, the grooves 49 may be configured to facilitate translation of the articulation catheter 37 therethrough.

Articulating catheter 37 includes a generally tubular configuration and may be made from any of the aforementioned materials described above with respect to that of links 32a' and 32b' (FIGS. 3-5). In the illustrated embodiment, articulating catheter 37 is made from a relatively elastic material to facilitate articulating the shaft 18 about the articulating section 23.

Articulating catheter 37 is configured to rotate each link 32b' of the links 32b thereabout. With this purpose in mind, articulating catheter 37 operably couples to the catheter rotation dial 42c by one or more suitable coupling methods and includes one or more splines 50 (FIGS. 3-5) extending along the length thereof. In the illustrated embodiment, the articulating catheter 37 includes a plurality of splines 50. The splines 50 are configured to couple to the grooves 49 to facilitate rotating each link 32b' simultaneously with respect to the links 32a when the articulating catheter 37 is rotated.

In the illustrated embodiment, the articulating catheter 37 is configured to house a driving structure, e.g., a drive rod 40 (FIGS. 1 and 3-4), therethrough to actuate the end effector 100, i.e., move one or both of the jaw members 16 and 14 from the open configuration (FIG. 1) to the clamping configuration (FIG. 2). In certain embodiments, the drive rod 40 may be configured to actuate one or more operable components associated with other types of end effectors, such as, for example, an end effector that includes a snare, loop, blade, stabilizer, etc. The articulating catheter 37 is configured to house a drive wire 53 (FIGS. 1, 3 and 4) that is operably coupled to a cutting element 55 (FIGS. 2 and 3) that is in operable communication with the jaw members 16 and 14. The drive wire 53 is translatable within the articulating catheter 37 to translate the cutting element 55 longitudinally through one or both of jaw members 16 and 14.

In certain embodiments, splines 50 are configured to facilitate translation of the articulating catheter 37 through the central annulus 38 when the shaft 18 is in an articulated configuration.

With reference to FIGS. 3-5 and 8B, tendons 34 are operably coupled to the links 32a. For illustrative purposes, four (4) tendons 34 are shown, as best seen in FIG. 8B. Tendons 34 are operable to produce additional structural compression loading between the links 32a and 32b, thereby maintaining the angle between the distal faces 35' and 43' when the links 32a and 32b are in either an articulated (FIG. 2) or non-articulated configuration (FIG. 1). Moreover, tendons serve as "short-section" beams preventing (or limiting) the relative rotation of one of the links 32b' with respect to another of the links 32b'. That is, the tendons 34 are configured as "pre-loaders" to create column stiffness of the links 32a and 32b.

Tendons 34 operably couple to the articulating dials 42a and 42b that are configured to actuate the tendons 34, i.e., "pull" the tendons 34, when the articulating dials 42a and 42b are rotated. This "pulling" effect tensions or "stiffens" the tendons 34 such that the tendons 34 facilitate maintaining the shaft 12 in one or more of articulation angles. The plurality of tendons 34 operably couple to the links 32a via one or more suitable coupling methods. More particularly, each link 32a' of the links 32a includes a corresponding plurality of first apertures or bores 36a (four (4) bores are shown in the representative figures) that are radially disposed along each of the links of the links 32a (as best seen in FIG. 6) and centrally aligned along a common axis. Each bore of the plurality of bores 36a is configured to receive a corresponding one of the tendons 34 therein, as best seen in FIG. 8B. A distal end of each of the tendons 34 is operably coupled to a distal most link of the links 32a by suitable methods, e.g., soldering.

In the illustrated embodiment, each link 32a' of the links 32a includes an optional second plurality of bores 36b (four (4) bores are shown in the representative drawings, see FIGS. 6 and 8A-8B). Each bore of the second plurality of bores 36b is configured to function as a passage for receiving corresponding electrical wiring (or other components) that requires communication with the jaw members 16 and 18 from the forceps 2.

The first and second pluralities of first and second bores 36a and 36b are disposed parallel with respect to the axis "B-B" of the central annulus (FIG. 6). Moreover, the first and second plurality of bores 36a and 36b are equally spaced-apart from each other along a radial circumference of each link 32a' of the links 32a (FIGS. 3 and 4).

With reference again to FIGS. 1 and 2, handle assembly 6 includes a fixed handle 24 and a movable handle 26. Fixed handle 24 is integrally associated with housing 4 and movable handle 26 is movable relative to fixed handle 24. Movable handle 26 of handle assembly 6 is ultimately connected to the drive assembly 9, which together mechanically cooperate to impart movement of one or both of the jaw members 14 and 16 to move from an open position (FIG. 1), wherein the jaw members 14 and 16 are disposed in spaced relation relative to one another, to a clamping or closed position, wherein the jaw members 14 and 16 cooperate to grasp tissue therebetween (FIG. 2).

Drive assembly 9 (FIGS. 1 and 2) including the drive rod 40 are in mechanical communication with the movable handle 26. More particularly, one or more gears, links, springs, or other component(s) that are operably supported and/or disposed within the housing 4 are configured to collectively provide translation of the drive rod 40 along the axis "A-A" as a result of proximal movement of the movable handle 26. Drive rod 40 may be made from any suitable material, e.g., metal. In certain embodiments, it may prove advantageous for the drive rod 40 to be relatively flexible. In this instance, the drive rod 40 may be made from a relatively flexible material, e.g., wire, band, cable, etc.

Jaw members 14, 16 are operatively and pivotably coupled to each other and located adjacent the distal end 20 of shaft 18 (FIGS. 1 and 2). For illustrative purposes, the end effector 12 is shown including a bilateral jaw configuration, i.e., both jaw members 14 and 16 are movable. However, the present disclosure contemplates that the end effector 12 may include a unilateral jaw configuration, i.e., jaw member 14 is movable with respect to jaw member 16 that is non-movable or stationary with respect to jaw member 14. Respective electrically conductive seal plates 5 and 7 are operably supported on and secured to jaw housings 28 and 30 of respective the jaw members 16 and 14.

Use of the forceps 2 is described herein in terms of an articulation sequence of the shaft 12.

In use, jaw members 14 and 16, initially, are in an open position (FIG. 1) and the shaft 12 is in a non-articulated configuration. That is, the articulation catheter 37 is in an initial, non-rotated configuration with the distal faces 43' of each of the links 32b' oriented parallel to the distal faces 35' of each link 32a', see FIG. 8A. As noted above, tendons 34 are provided to maintain the distal faces 43' of each of the links 32b' parallel to the distal faces 35' of each of the links 32a'. That is, the tendons 34 are "loaded" under a predetermined pulling or "stiffening" force provided by one or both of the dials 42a and 42b.

To position the jaw members 14 and 16 adjacent target tissue, one or both of the articulation dials 42a and 42b may be rotated to release tendons 34 from the "loaded" configuration. Subsequently, the articulation dial 42c may be rotated, e.g., approximately 180° in either the clockwise or counter clockwise direction. As noted above, the links 32a' and links 32b' are configured to function as "swash cams" and "cam followers", respectively. In accordance with the present disclosure, rotation of the catheter rotation dial 42c rotates the links 32b simultaneously in either the clockwise or counter clockwise direction. As each link 32b' of the links 32b rotates, the distal face 43' rotates with respect to the distal face 35' of each link 32a' of the links 32a'. When the distal face 43' has been rotated approximately 180° the distal face 43' will be oriented coincident with respect to the distal face 35' of the links 32a' (FIG. 8B). In the illustrated embodiment, this 180° rotation of the articulation dial 42c results in an articulation angle of the shaft 12 being approximately equal to 15°, as best seen in FIG. 2.

To lock the shaft 12 in the articulated configuration, one or both of the dials 42a and 42b may be rotated. Rotating the dials 42a and 42b re-establishes tension in the tendons 34, thus, causing compression of the links 32a and 32b, friction, and moment reaction loading therebetween, which, in turn, prevents and/or inhibits links 32a and 32b from tilting and, thus, the shaft 12 from moving. When the articulating section 23 is in the locked configuration, the tendons 34 are in a loaded state, but not under the high tension as is typically the case with conventional shafts 12 that are configured to articulate. That is, tension of the tendons 34 is lower due to the structural contacts, i.e., the links 32a and 32b, taking the bending or articulating loads.

From the foregoing and with reference to the various figure drawings, those skilled in the art will appreciate that certain modifications can also be made to the present disclosure without departing from the scope of the same. For example, in certain instances, to simplify manufacture of the shaft 18, it may prove advantageous to have a shaft with an articulating portion that includes a compliant cylindrical extrusion. In this instance, the entire shaft 18 may be made from a compliant extrusion. An interior of the shaft 18 may include apertures or lumens that are formed during the extrusion process of the shaft 18. The lumens take the place of the first and second plurality of bores 36a and 3b. To this end, the lumens may extend along a length of the shaft 18 such that a desired amount of articulation may be achieved.

It is contemplated that one or more resilient members, e.g., a spring, may be operably associated with the tendons 34 and/or the dials 42a and 42b to facilitate tensioning or stiffening the tendons 34.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic instrument, comprising:
   a housing having a shaft extending therefrom that defines a longitudinal axis therethrough, the shaft including an articulating section, the articulating section having a plurality of stationary and rotatable links arranged in an alternating configuration along the articulating section, each rotatable link of the plurality of rotatable links rotatably seated within a corresponding stationary link of the plurality of stationary links to collectively define a central annulus therethrough;
   an end effector assembly operatively connected to a distal end of the shaft including a pair of first and second jaw members; and
   an articulation catheter operably disposed through the central annulus and configured to rotate the rotatable links with respect to the stationary links to articulate the shaft about the articulating section,
   wherein each stationary link of the plurality of stationary links includes a proximal face and a distal face, wherein the proximal face is perpendicular to the central annulus and the distal face is oriented at an angle that is different from the proximal face,
   wherein each rotatable link of the plurality of rotatable links includes a proximal face and a distal face, the proximal face of each rotatable link rests at least partially along a corresponding distal face of each stationary link such that rotation of the plurality of rotatable links cams the plurality of rotatable links to articulate the shaft about the articulating section.

2. An endoscopic instrument according to claim 1, wherein each stationary link of the plurality stationary links includes a first plurality of bores configured to receive a corresponding plurality of tendons therethrough, the plurality of tendons configured to maintain the plurality of stationary links and rotatable links in a relatively fixed configuration with respect to one another.

3. An endoscopic instrument according to claim 1, wherein each proximal and distal face of each stationary link of the plurality of stationary links includes a counter bore defined therein that is concentric to the proximal and distal faces for interfacing with a respective rotatable link of the plurality of rotatable links.

4. An endoscopic instrument according to claim 3, wherein the counter bore on each proximal and distal face of each stationary link of the plurality of stationary links includes the same depth and diameter.

5. An endoscopic instrument according to claim 1, wherein each stationary link of the plurality of stationary links is configured such the distal faces thereof are parallel with respect to one another when the shaft is in a non-articulated configuration.

6. An endoscopic instrument according to claim 2, wherein each rotatable link of the plurality of rotatable links is cylindrical about an outer diameter thereof that is smaller than a diameter formed by the plurality of tendons such that the plurality of rotatable links are positionable within the plurality of tendons.

7. An endoscopic instrument according to claim 3, wherein the proximal face of each rotatable link of the plurality of rotatable links is perpendicular to the central annulus and the distal face of each rotatable link of the plurality of rotatable links is angled with respect to the proximal face of each rotatable link of the plurality of rotatable links.

8. An endoscopic instrument according to claim 7, wherein the angles of the distal faces of the stationary links and the rotatable links are equal to one another.

9. An endoscopic instrument according to claim 7, wherein the corresponding counter bores on each of the proximal and distal faces of each link of the plurality of stationary links is configured for interfacing with a corresponding cylindrical boss concentrically disposed on each of the proximal and distal faces of each rotatable link of the plurality of rotatable links.

10. An endoscopic instrument according to claim 1, wherein an interior surface of each rotatable link of the plurality of rotatable links defines at least one groove extending therein, the at least one groove is parallel to the longitudinal axis.

11. An endoscopic instrument according to claim 10, wherein the articulating catheter includes at least one spline extending along the length thereof, the at least one spline configured to couple to the at least one groove on the interior surface of each rotatable link of the plurality of rotatable links to facilitate rotating each rotatable link of the plurality of rotatable links simultaneously with respect to the plurality of stationary links.

12. An endoscopic instrument according to claim 10, wherein an interior surface of each rotatable link of the plurality of rotatable links defines a plurality of grooves extending therein, the plurality of grooves being parallel to the longitudinal axis.

13. An endoscopic instrument according to claim 12, wherein the articulating catheter includes a plurality of splines extending along the length thereof, each spline of the plurality of splines configured to couple a corresponding groove of the plurality grooves on the interior surface of each of the rotatable links of the plurality of rotatable links to facilitate rotating the plurality of rotatable links with respect to the plurality of stationary links.

14. An endoscopic instrument according to claim 1, wherein the articulating catheter includes a generally tubular configuration and is made from a relatively elastic material to facilitate articulating the shaft about the articulating section.

15. An endoscopic instrument according to claim 1, wherein the articulating catheter is configured to house a driving structure therethrough to actuate the end effector assembly.

16. An endoscopic instrument according to claim 1, wherein a rotating dial is supported on the housing and configured to rotate the articulation catheter.

17. An endoscopic instrument according to claim 1, wherein each stationary link of the plurality of stationary links includes a second plurality of bores defined therein and configured to receive a corresponding plurality of electrical leads therethrough to connect to the end effector assembly.

18. An endoscopic instrument according to claim 1, wherein each stationary link of the plurality of stationary links and each rotatable link of the plurality of rotatable links includes an annular configuration.

19. An endoscopic forceps, comprising:
a housing having a shaft extending therefrom that defines a longitudinal axis therethrough, the shaft including an articulating section disposed thereon, the articulating section having a plurality of stationary and rotatable links arranged in an alternating configuration along the articulating section, each rotatable link of the plurality of rotatable links rotatably seated within a corresponding stationary link of the plurality of stationary links to collectively define a central annulus therethrough,;
an end effector assembly operatively connected to a distal end of the shaft for treating tissue includes a pair of first and second jaw members, at least one of the first and second jaw members movable relative to other jaw member from an open position, wherein the first and second jaw members are disposed in spaced relation relative to one another, to a clamping, position, wherein the first and second jaw members cooperate to grasp tissue therebetween; and
an articulation catheter operably disposed through the central annulus and configured to rotate the rotatable links with respect to the stationary links to articulate the shaft about the articulating section,
wherein the articulating catheter is configured to house a drive wire that is operably coupled to a cutting element in operable communication with the first and second jaw members, the drive wire translatable within the articulating catheter to translate the cutting element longitudinally through at least one of first and second jaw members,
wherein each stationary link of the plurality of stationary links includes a proximal face and a distal face, wherein the proximal face is perpendicular to the central annulus and the distal face is oriented at an angle that is different from the proximal face,
wherein each rotatable link of the plurality of rotatable links includes a proximal face and a distal face, the proximal face of each rotatable link rests at least partially along a corresponding distal face of each stationary link such that rotation of the plurality of rotatable links cams the plurality of rotatable links to articulate the shaft about the articulating section.

* * * * *